United States Patent
Ohlendorf et al.

(10) Patent No.: US 10,327,630 B2
(45) Date of Patent: Jun. 25, 2019

(54) METHOD AND SYSTEM FOR DETERMINING THE SUBJECTIVE REFRACTION PROPERTIES OF AN EYE

(71) Applicant: Carl Zeiss Vision International GmbH, Aalen (DE)

(72) Inventors: Arne Ohlendorf, Tübingen (DE); Siegfried Wahl, Donzdorf (DE); Jesús-Miguel Cabeza Guillén, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 15/934,263

(22) Filed: Mar. 23, 2018

(65) Prior Publication Data

US 2018/0214020 A1  Aug. 2, 2018

Related U.S. Application Data

(63) Continuation of application No. PCT/EP2016/072607, filed on Sep. 22, 2016.

(30) Foreign Application Priority Data

Sep. 23, 2015 (DE) .......................... 10 2015 116 110

(51) Int. Cl.
*A61B 3/028* (2006.01)
*A61B 3/00* (2006.01)
(Continued)

(52) U.S. Cl.
CPC .......... *A61B 3/0285* (2013.01); *A61B 3/0041* (2013.01); *A61B 3/032* (2013.01); *A61B 3/04* (2013.01)

(58) Field of Classification Search
CPC ..... A61B 3/0285; A61B 3/0041; A61B 3/032; A61B 3/022; A61B 3/02; A61B 3/028
(Continued)

(56) References Cited

U.S. PATENT DOCUMENTS

| 4,929,076 A | 5/1990 | Masuda et al. |
| 5,026,151 A | 6/1991 | Waltuck et al. |

(Continued)

FOREIGN PATENT DOCUMENTS

| CN | 102596005 A | 7/2012 |
| DE | 4091126 C2 | 7/1996 |

(Continued)

OTHER PUBLICATIONS

Espacenet Machine Translation of DE19633062.*
(Continued)

*Primary Examiner* — Collin X Beatty
(74) *Attorney, Agent, or Firm* — Ewers & Hasselmann PLLC

(57) ABSTRACT

A system determines the subjective refraction properties of an eye of a test subject perceiving a natural image. The system contains a memory in which at least one natural image is stored; a display device for displaying the at least one natural image from the memory; and a lens arrangement for adjusting various light-refracting elements in an optical path between the eye of the test subject and the display device. The lens arrangement is arranged at a predefined distance from the display device. A corresponding method and the use of a natural image for refraction determination are also disclosed.

19 Claims, 6 Drawing Sheets

(51) Int. Cl.
*A61B 3/032* (2006.01)
*A61B 3/04* (2006.01)

(58) Field of Classification Search
USPC .................. 351/216, 246, 211, 239, 233
See application file for complete search history.

(56) References Cited

U.S. PATENT DOCUMENTS

| | | | |
|---|---|---|---|
| 6,325,513 | B1 | 12/2001 | Bergner et al. |
| 6,761,454 | B2 | 7/2004 | Lai et al. |
| 7,771,052 | B2 | 8/2010 | Kratzer et al. |
| 8,708,490 | B2 | 4/2014 | Baranton et al. |
| 2008/0137037 | A1 | 6/2008 | Kratzer et al. |

FOREIGN PATENT DOCUMENTS

| | | |
|---|---|---|
| DE | 19516745 A1 | 11/1996 |
| DE | 19537499 A1 | 3/1997 |
| DE | 19633062 A1 | 2/1998 |
| DE | 102004055754 A1 | 5/2006 |
| JP | 11028187 A | 2/1999 |
| JP | 2004275591 A | 10/2004 |
| JP | 2005253503 A | 9/2005 |
| JP | 2012040430 A | 3/2012 |
| WO | 2007026368 A2 | 3/2007 |

OTHER PUBLICATIONS

Field "Relations between the statistics of natural images and the response properties of cortical cells," vol. 4, No. 12, Journal of the Optical Society of America, 1987.
Tolhurst et al. "Amplitude spectra of natural images," Ophthal. Physiol. Opt., vol. 12, 1992.
Masaoka et al. "Sensation of Realness From High-Resolution Images of Real Objects," IEEE Transactions on Broadcasting 59(1):72-83, Mar. 2013.
English-language translation of examination report by the DPMA (German Patent and Trademark Office) issued in DE 10 2015 116 110.9, to which this application claims priority, dated May 2, 2016.
International Search Report issued in PCT/EP2016/072607 (of which this application is a continuation) and English-language translation thereof, dated Jan. 19, 2017.
International Preliminary Report on Patentability issued in PCT/EP2016/072607 (of which this application is a continuation) and English-language translation thereof, dated Jan. 22, 2018.
Kannon et al.: "Effects of Blur Adaption on Spatial Frequency Transfer Characteristics of Visual Perception," The IEICE transactions D, 2007, vol. J90-D, No. 7, pp. 1812-1819, along with English-language abstract and Machine Translation.
Office action by the Japanese Patent Office in JP 2018-523797, which is a counterpart of this application, dated Sep. 18, 2018, along with English-language summary and Machine translation.
Office action by the National Intellectual Property Adminstration, P.R. China in CN 201680055653.7, which is a counterpart of this application, dated Dec. 3, 2018, along with an English-language translation.

\* cited by examiner (Related Art)

METHOD AND SYSTEM FOR DETERMINING THE SUBJECTIVE REFRACTION PROPERTIES OF AN EYE

CROSS REFERENCE TO RELATED APPLICATIONS

This application is a continuation application of International Application No. PCT/EP2016/072607 filed on Sep. 22, 2016, and claims priority to German patent application DE 10 2015 116 110.9 filed on Sep. 23, 2015, both of which are hereby incorporated by reference in their entireties.

TECHNICAL FIELD

The present disclosure relates to a system for determining the subjective refraction properties of the eye of a subject based on the use of a natural image. The present disclosure furthermore relates to methods for determining the subjective refraction properties of an eye of a subject based on the use of a natural image or a natural scenery, and to the use of a natural image to determine the subjective refraction properties of an eye of a subject.

BACKGROUND

For the subjective refraction determination, examination devices such as measuring spectacles or phoropters are known, in which, for example, spherical or cylindrical testing lenses are pivoted in front of a subject's eye to determine the refractive error of the subject on the basis of his (or her) statements.

In the subjective refraction determination in accordance with national and international standards, defined vision symbols, also known as optotypes, are always used. The optotypes are shown in black on a white background with a high contrast. The stroke width (⅕ of the type size) of the Landolt ring, which is accepted as a standardized DIN vision symbol, is such that, in a row intended for visual acuity 1, it appears to the eye at an angle of 1 arc minute. Further vision symbols are the tumbling E, which is frequently used to examine children. In examinations of near visual acuity, a letter chart is frequently used, for example what are known as Nieden reading charts. The optotypes are represented individually or in rows of 5 or 10 optotypes.

For the refraction determination, optotypes of different sizes are successively shown to the subject at a defined distance. For this, the subject sits at a predetermined distance from the displayed optotypes. The defects of the eyes are determined by approaching the threshold of the resolution capability of the subject.

Document U.S. Pat. No. 6,325,513 describes as a disadvantage in the related art the fact that the subject, in the case of such a measurement, does not assume a relaxed posture and the natural visual impression is falsified. For this reason, the document proposes a type of compact measuring spectacles, in which the symbols for refraction determination are projected onto the retina. With the solution proposed therein, superposition of produced measurement images with the environment is made possible with a comfortable, relaxed sitting posture. The subjective refraction determination is affected with reference to the optotypes.

Document U.S. Pat. No. 5,026,151 A discloses an apparatus for binocular eyesight testing having a display apparatus, on which eyesight test symbols may be represented for the left and the right eye in alternation. A controllable closure device is provided herefor, which is controlled such that some of the represented eyesight test symbols are shown only to the left eye, some of the represented eyesight test symbols are shown only to the right eye, and some of the eyesight test symbols are shown to both eyes. This makes possible binocular eyesight testing. The display apparatus can be a television monitor having a sufficiently high frame rate. However, a television monitor typically does not have a sufficiently high luminance to represent the separate vision symbols for each individual eye at the required luminance (for example 250 cd/m$^2$).

SUMMARY

Against this background, it is an object of the present disclosure to provide a system and a method for determining the subjective refraction properties of an eye of a subject, which further improve the refraction determination and in particular permit a meaningful determination of the habitual refractive errors.

In accordance with a first aspect of the disclosure, it is therefore proposed to provide a system for determining the subjective refraction properties of an eye of a subject based on the use of a natural image, wherein the system includes the following:
- a memory device, in which at least one natural image is stored;
- a display apparatus for displaying the at least one natural image from the memory device; and
- an optics arrangement for setting different light-refracting elements into an optical path between the subject's eye and the display apparatus, wherein the optics arrangement is arranged at a specified distance from the display apparatus.

It has been found that the traditional representation of vision symbols does not always give an optimum result in the determination of the habitual refraction. Traditional optotypes in accordance with national and international standards, which are used when measuring the refractive errors of the eyes under monocular or binocular conditions and during the MKH-Haase method (Measuring and Correcting Methodology after Haase), are presented in accordance with the respective standards. However, these standardized conditions generally do not correspond to the conditions that a subject would encounter in everyday life.

It is proposed within the context of the present disclosure to use a natural image for the subjective refraction determination, in particular a natural scenery, such as a photo of a landscape. Here, a natural image is typically distinguished by a spatial frequency distribution resulting from the edges of the objects represented in the image and typically a spatial-frequency-dependent contrast, wherein the contrast decreases in particular as the spatial frequency increases. The contrast range of a natural image used in the context of the present disclosure, i.e., the range of contrasts occurring in the natural image, in a determination of the contrast in accordance with Michelson, is typically from 0.2 (inclusive) to 1 (inclusive), more typically 0.3 (inclusive) to 1 (inclusive), and even more typically from 0.4 (inclusive) to 1 (inclusive).

The spatial frequency is a measure of how often sinusoidal components of an image repeat. If the distance between the sinusoidal components of an image is very large, this corresponds to a low spatial frequency and a coarse structure. If, by contrast, the distance between the sinusoidal components is low, this corresponds to a high spatial frequency and a fine detail. If the distance from the display apparatus changes, the specific spatial frequencies of the observed image also change. It is therefore understood that a spatial frequency with reference to a length and/or pixels of a screen having a defined size depend on the observation distance d from the display device. However, the spatial frequency can also be converted and given as a distance-independent value in cycles per degree, also referred to as cpd. Spatial frequency is understood to mean the number of edges per degree of visual angle.

In addition to its spatial representation, for example in the form of a matrix of pixels of different gray or color levels, an image can also be described by the spatial frequencies contained therein. In simplified terms, a small spatial frequency corresponds to a larger structure. A high spatial frequency corresponds to a smaller structure. The spatial frequency is therefore a measure of the size of a depicted structure.

When using optotypes, it is furthermore the subject's desire to always give the correct answer. This produces a type of testing situation, in which the subject possibly puts pressure on himself. The solution space of correct answers for vision symbols, such as for example the tumbling E and its four possible orientations, is limited. The subject can momentarily squint to force the identification of the correct result.

Furthermore, a subject possibly will not assume his typical head and body posture but sit in an unnatural or tense position. This can also result in visual impressions being perceived in a different manner and in the worst case negatively affect the ascertained strength. Consequently, deviations between the results of a subjective refraction determination and the habitual refractive errors of the subject may occur.

In the solution described here, it is therefore proposed to perform the determination of the subjective refraction properties of the subject's eye with reference to natural images having defined features. Natural images can here be photographs or depictions of a natural scenery, in particular of a typical environment in which one lives. The refraction determination can be tailored to the daily vision conditions of the subject on the basis of the contents shown in the natural images. A further advantage of this solution over vision symbols is that the subject does not already know which answer he is expected to give.

On the basis of the natural images, it is possible to determine the habitual refractive errors of the eyes by approximation to the threshold of the resolution capability. To this end, the natural image has various features of different structure sizes or spatial frequencies. Viewed at the specified distance from the display apparatus, the features of different sizes correspond to different observation angles, which are used in turn to determine the resolution capability. For example, it is possible to test whether the subject can detect, or with which light-refracting elements in the optical path the subject can detect, a structure, such as a tree or a rock formation. The same is true for a natural scenery of a test environment.

The optics arrangement serves for introducing different light-refracting elements, such as spherical or cylindrical test lenses, into the optical path between the subject's eye and the display apparatus. The optics arrangement can be, for example, a phoropter or measuring spectacles.

In accordance with a second aspect of the present disclosure, a system for determining the subjective refraction properties of an eye of a subject based on the use of an image is proposed, wherein the system includes the following:
a memory device, in which at least one image having a plurality of image regions is stored, wherein different image regions have different, in particular increasing, spatial frequencies and wherein different image regions have a spatial-frequency-dependent contrast that decreases as the spatial frequency increases;
a display apparatus for displaying the at least one, in particular natural, image from the memory device;
an optics arrangement for setting different light-refracting elements into an optical path between the subject's eye and the display apparatus, wherein the optics arrangement is arranged at a specified distance from the display apparatus.

In accordance with a third aspect of the disclosure, the use of a natural image for determining the subjective refraction properties of an eye of a subject, having a plurality of image regions, is proposed, wherein different image regions have different, in particular increasing, spatial frequencies and wherein the natural image depicts a natural scenery.

In accordance with a fourth aspect of the disclosure, a method for determining the subjective refraction properties of an eye of a subject based on the use of a natural image is proposed, wherein the method includes the following steps:
providing a system for determining the subjective refraction properties of an eye of a subject based on the use of a natural image, wherein the system includes the following:
a memory device, in which at least one natural image is stored;
a display apparatus for displaying the at least one natural image from the memory device;
an optics arrangement for setting different light-refracting elements into an optical path between the subject's eye and the display apparatus;
displaying the at least one natural image, which is stored in a memory device, on the display apparatus; and
setting different light-refracting elements into the optical path between the subject's eye and the display apparatus using the optics arrangement, wherein the optics arrangement is arranged at a specified distance from the display apparatus.

In accordance with a fifth aspect of the disclosure, a method for determining the subjective refraction properties of an eye of a subject based on the use of a natural image is proposed, wherein the method includes the following steps:
providing a system for determining the subjective refraction properties of an eye of a subject based on the use of a natural image, wherein the system includes the following:
a memory device, in which at least one image having a plurality of image regions is stored, wherein different image regions have different spatial frequencies and wherein the natural image depicts a natural scenery;
a display apparatus for displaying the at least one natural image from the memory device;
an optics arrangement for setting different light-refracting elements into an optical path between the subject's eye and the display apparatus; and
displaying the at least one natural image, which is stored in a memory device, on the display apparatus;
setting different light-refracting elements into the optical path between the subject's eye and the display apparatus using the optics arrangement, wherein the optics arrangement is arranged at a specified distance from the display apparatus.

In accordance with a sixth aspect of the disclosure, a method for determining the subjective refraction properties of an eye of a subject based on the use of a natural scenery is proposed, wherein the method includes the following steps:

providing a test environment having a natural scenery, wherein the natural scenery, as viewed from a specified position (P), has different regions of different spatial frequencies;

providing an optics arrangement for setting different light-refracting elements into an optical path between the subject's eye and the natural scenery; and setting different light-refracting elements into the optical path between the subject's eye and the natural scenery using the optics arrangement, wherein the optics arrangement is arranged at the specified position.

The advantages described in detail above for the first aspect of the disclosure apply accordingly to the further aspects of the disclosure.

The refraction determination can be further improved with the proposed solutions because it is possible to perform a habitual refraction determination under conditions that are more like the natural vision conditions of the subject.

The object stated at the outset is therefore achieved in full.

In one exemplary embodiment of the system, the natural image, or an image region of the natural image, can have a spatial-frequency-dependent contrast, wherein the contrast decreases as the spatial frequency increases.

In other words, at least one region of the natural image or image for determining the subjective refraction properties of the eye can have a contrast which is greater at low spatial frequencies than at high spatial frequencies. A low spatial frequency here corresponds to a larger structure. A high spatial frequency here corresponds to a smaller structure. In this context, the term natural image can refer to an image that has at least one image region with a spatial-frequency-dependent contrast, wherein the contrast decreases as the spatial frequency increases. By contrast, the optotypes in conventional eyesight testing charts in accordance with national and international standards have a constant contrast independently of the structure size or spatial frequency. In conventional eyesight testing charts, large and small optotypes are typically represented in black on a white background. The representation of an optotype on a conventional eyesight testing chart consequently has, independently of the spatial frequency, a constant contrast in accordance with Michelson having a constant value of between 0.9 and 1. By contrast, the contrast range of a natural image used in the context of the present disclosure in a determination of the contrast in accordance with Michelson is typically from 0.2 (inclusive) to 1 (inclusive), more typically 0.3 (inclusive) to 1 (inclusive), and even more typically from 0.4 (inclusive) to 1 (inclusive).

The contrast is typically inversely proportional to the spatial frequency. At least sectionally, the relationship K(f) ~1/f, or more generally K(f)~$f^a$ with $-1.5 \leq a \leq -0.8$, in particular a=−1.2, can apply. Conventional eyesight testing charts, by contrast, having for example black eyesight test symbols on a white background, have a constant contrast with respect to the spatial frequency. This is to ensure maximum discernability of the optotypes in conventional eyesight testing charts. However, it has unexpectedly been found that the use of natural images, for example a natural scenery or images for determining the subjective refraction properties of an eye, which have at least in subregions a spatial-frequency-dependent contrast that decreases as the spatial frequency increases, can provide a result which exceeds a conventional refraction determination. In particular, subjects may feel that a visual aid that is adapted based on such a result of the refraction determination is more comfortable in daily life.

The contrast or photometric contrast can be understood to be a difference in luminance. The contrast can be determined between spatially more or less neighboring stimuli. In accordance with Michelson, the contrast $K_M$ for grating patterns is defined by $$K_M = \frac{L_{Max} - L_{Min}}{L_{Max} + L_{Min}} \quad (1)$$

wherein $L_{Max}$=luminance density maximum and $L_{Min}$=luminance density minimum. In this case, the contrast at a fixed, average brightness varies by increasing or lowering the brightness by the same amount. However, if small vision objects, such as for example Landolt rings, are used, the contrast can be defined in accordance with Weber by $$K_W = \frac{L_I - L_U}{L_U} \quad (2)$$

with $L_I$=luminance density inner field and $L_U$=luminance density outer field. For examination of the visual acuity, the contrast is defined in accordance with Weber. Statements in this disclosure relate to the definition of contrast in accordance with Michelson (see also Bex. et al. "Spatial frequency, phase, and the contrast of natural images," Journal of the Optical Society of America, Vol. 19, No. 6, 2002).

Typically, a contrast of the natural image is elevated for higher spatial frequencies, in particular to a contrast level of a natural scenery depicted by the natural image.

By increasing a contrast for higher spatial frequencies, a low-pass characteristic of an imaging system during the image recording of the natural image can be compensated. One advantage of this configuration is that, if the natural image is observed on a display apparatus, the visual impression that is brought about is similar to the one the subject would have were he observing a natural scenery directly rather than a depiction of the natural scenery.

In one exemplary embodiment of the system, provision may be made for the natural image, or the natural scenery that is depicted therein, to be a depiction of a typical environment.

One advantage of this exemplary embodiment is that the subject looks at contents to which he is accustomed and, as a result, is better able to disassociate himself psychologically from the testing situation. The subject will therefore generally assume a more relaxed posture. Natural images can typically correspond to depictions, in particular photographs or photorealistic or rendered depictions, of the typical environment in which one lives. For instance, images of landscapes can be shown to a subject. For example, a natural image can be a photograph or photorealistic depictions of a landscape scene, such as a contiguous representation of a scene of a landscape, in particular with landscape-typical flora and fauna. Natural images can therefore be an environment of the subject to which he is accustomed. Hereby, it is sometimes possible to achieve better results in the habitual refraction determination, because a typical vision situation forms the basis of the refraction determination. Furthermore, natural images can be selected such that they bring about positive associations in the subject, such as images of a beach, a forest or the like.

In a further configuration of the system, provision may be made for the natural image to have features for determining the subjective refraction properties.

Provision may be made in particular in one configuration of the system for the natural image to have at least two regions having different spatial frequencies. Regions having different spatial frequencies serve for testing visual acuity. To be able to resolve small structures, that is to say structures having a high spatial frequency, great visual acuity is necessary. It is possible to define in a natural image what are known as "regions of interest" (ROIs) that belong to a specific range of spatial frequencies which corresponds to a specific visual acuity. In other words, regions for testing can be ROIs representing regions in a natural image that contain a range of spatial frequencies. Defects of the eyes are determined by approaching the natural threshold of the resolution capability. A high spatial frequency here corresponds to a small structure size. The subject can be asked to name features from regions having different spatial frequencies, typically having spatial frequencies that become ever greater, that is to say relatively small structure sizes or objects, until he reaches the threshold of his resolution capability. The contrast for regions having increasing spatial frequencies typically decreases. The contrast can in particular be inversely proportional to the spatial frequency.

In a further exemplary embodiment of the system, provision may be made for the natural image to have a distribution of spatial frequencies comprising a plurality of, typically all, spatial frequencies required for determining subjective refraction properties of the subject's eye in one image.

In other words, the natural image typically has a specified distribution of spatial frequencies that is great in dependence on the detailed fidelity and decreases as the detail fidelity decreases. As a result, all thresholds for the determination of the refractive errors can typically be presented simultaneously in one image. One advantage of this exemplary embodiment is that only a single image can be used for the refraction determination. By way of example, a skyscraper scene can include buildings as the largest elements, vehicles as medium-sized elements, down to billboards with individual letters as small elements. Further incremental steps are of course possible. Shown in another example is a nature scene with mountain ranges down to leaves or fir needles. In contrast to conventional eyesight testing charts, the natural image is typically not set up such that the size of the image elements becomes ever smaller in one direction, for example from top to bottom. In particular, a series of sizes does not monotonously increase or decrease in one direction. The distribution of spatial frequencies in the image can in particular be pseudorandom. Consequently, the distribution does not follow a scheme that would be immediately discernible by the subject. Optotypes or individual optotypes can optionally be presented in augmented fashion, in particular embedded in such a scene.

In a further exemplary embodiment of the system, provision may be made for the natural image to depict structures with different spatial frequencies (f), wherein the spatial frequency distribution, upon observation at the specified distance, typically has at least a spatial frequency of less than or equal to 0.3 and at least a spatial frequency greater than or equal to 60 cycles per degree, more typically at least a spatial frequency of less than or equal to 0.01 and at least a spatial frequency greater than or equal to 80 cycles per degree.

The spatial frequency distribution is typically given in cycles per degree, i.e., as a spatial frequency with respect to an angle, since the visual acuity of the subject can be considered to be a measure of the angular resolution capability. The angle, in turn, can be calculated from the specified distance, from which the subject views the display apparatus, and the size of the structure displayed on the display apparatus. By way of example, the natural image can have a spatial frequency distribution of 0.009 to 85 cycles per degree. In another example, the natural image can have a spatial frequency distribution of 0.02 to 70 cycles per degree. This consequently gives the relationship of lower value≤given range≤upper value. The structures in the interval in-between can exhibit an arbitrary number of spatial frequencies. A structure having a spatial frequency in the present case is understood to mean a structure having a spatial size that corresponds to the spatial frequency.

In a further exemplary embodiment of the system, provision may be made for the system to additionally have a selection device for selecting the natural image according to the preferences of the subject.

One advantage of this exemplary embodiment is that the refraction determination can be adapted to a typical environment of the subject, for example in terms of illumination, contrast, color spectrum and the contents that are represented. It is typically possible to take into account in this way the neuronal transfer function of the subject in the refraction determination. By way of example, an environment which is natural for the subject, such as an urban environment, a forest, a beach, can be selected. Another advantage can be seen in that the subject is more relaxed in the measurement situation, and as a result more realistic values for the subjective refraction properties of his eye can be obtained.

In a further exemplary embodiment of the system, provision may be made for the natural image to have at least one alien component.

An alien component can be, for example, a computer-graphic change. One advantage of this configuration can be seen in that it is possible to thwart expectations for the detection of details in natural images. Unexpected details can be depicted, such as for example a specific shape of cloud, oak leaves on a maple tree, or an unexpected shape of a tree trunk. Here, too, the preferences of the subject can be advantageously taken into consideration by playing with the expectations of the subject and employing in a targeted fashion alien components that this subject did not expect.

In a further exemplary embodiment of the system, provision may be made for at least one vision symbol to be at least partially integrated in the natural image.

Vision symbols, or their geometries, indicated in national and international standards for determining the subjective refraction, can typically be incorporated entirely or partially in the natural image. For example, distances or stroke thicknesses of features of the natural image can correspond to those of standardized vision symbols.

In a further exemplary embodiment of the system, provision may be made for the display apparatus to have a curved display surface.

A curved screen is suitable because it corresponds to the anatomical conditions of the eye having a curved retina. Representation on a conventional, flat screen is nevertheless also common. To enable an approximation to the anatomical conditions of the eye, the representation of the natural images typically takes place on a curved display unit having in particular a screen diagonal of 55 inches or more, so as to provide an immersive feel and thus a more natural visual impression in the refraction determination. However, the use of conventional monitors is not excluded. Representation using a projector onto straight or curved surfaces in space is also feasible. The use of a virtual reality (VR) system having a typically large field of view and an adjustable focus area from close distances to virtual distances in the far range and optionally integrated phoropter or adaptive optical unit is also feasible. If the display surface is curved, the distance from the eye of the observer can be individually determined for each point of the display surface. For simplification purposes, the distance from the center of curvature can be considered. Holographic glasses can also be used.

In a further exemplary embodiment of the system, provision may be made for the determination of the subjective refraction properties to be affected in monocular fashion in two-dimensional space or in monocular fashion under binocular conditions.

The refraction determination can therefore be affected under two-dimensional or three-dimensional conditions. In the refraction determination and the binocular conditions in three-dimensional space, polarization filters can be used, for example, to separate the contributions for the right and left eye.

In a further exemplary embodiment of the system, provision may be made for the system to furthermore have means for capturing the head movement and/or eye movement of the subject.

If, in accordance with this exemplary embodiment, a means for measuring the eye movements is integrated in the system, it is possible by analyzing the distribution of the eye movements on the image viewed to track typically in real time which spatial frequencies are frequently viewed. It is possible to derive therefrom which spatial frequencies are frequently detected. This in turn can be used to precisely define the resolvable threshold of the eye with and without spectacles. The subjective refraction properties of the eye can be determined by successively introducing with the optics arrangement different light-refracting elements (e.g., spherical lenses etc.) and in each case determining the resolvable threshold of the eye. This can be repeated until a refractive error has been corrected. One advantage of this configuration is that the determination of refraction parameters of the subject can be affected without his express feedback. This is advantageous in particular in subjects that are unable to articulate, or unable to articulate adequately, such as for example in the case of children or subjects having impairments. If the head movements of the subject are captured, this allows the image to be viewed to be adapted to the head movements of the subject in real time, while his refraction is determined.

In a further exemplary embodiment of the system, provision may be made for the natural image to be a moving image or video.

One advantage of this configuration is that the measurement situation can be de-stressed so that the refraction determination can be performed with a more relaxed subject. The results consequently are more likely to correspond to the natural vision conditions. Moving images can be a two-dimensional or three-dimensional video, which is presented to the subject during the habitual refraction determination.

In a further exemplary embodiment of the system, provision may be made for the system to furthermore have an eccentric photorefractor.

During the refraction determination, a continuous measurement of the refractive errors can typically be performed for example by way of eccentric photorefraction. An examiner can here for example track the residual refraction of the eye on his (or her) screen and check the quality of his refraction during the determination. The eccentric photorefractor is typically arranged at the same distance as the display apparatus on which the natural image is presented. Alternatively, the photorefractor can be provided with or as part of the optics arrangement. The optics arrangement can therefore include an eccentric photorefractor.

The ascertainment of the habitual refraction errors using natural images can be typically integrated in a known subjective method, such as using measuring spectacles, or a manual or digital phoropter.

By way of example, it is possible to perform one step or a plurality of the following steps of the refraction determination with image contents from natural images: determining a best spherical lens, determining an astigmatism, axis alignment of an astigmatism, strength adjustment of an astigmatism and monocular and/or binocular spherical fine adjustment (red/green). During this process, the subject is looking at the display apparatus on which the natural image is represented. To measure the habitual refractive error, the subject must assess, read out, or identify image contents, such as trees, branches, or leaves in an image of a landscape, so that a spherical and possibly also astigmatic error of the eye can be determined and consequently also corrected. The aim of the refraction determination can here be the correction of the habitual subjective refraction properties with the maximally detectable spatial frequency at maximum positive correction.

It goes without saying that the aforementioned features and those yet to be explained below can be used not only in the combination specified in each case but also in other combinations or on their own, without departing from the scope of the present disclosure. In particular, the above-mentioned configurations and developments apply not only to natural images but also correspondingly to the above-described further aspects of the disclosure and also to a test environment, in particular with a natural scenery.

BRIEF DESCRIPTION OF THE DRAWINGS

Below, advantageous exemplary embodiments of the disclosure, which are schematically depicted in the drawings, are described, wherein.

DESCRIPTION OF EXEMPLARY EMBODIMENTS

Figure 1:
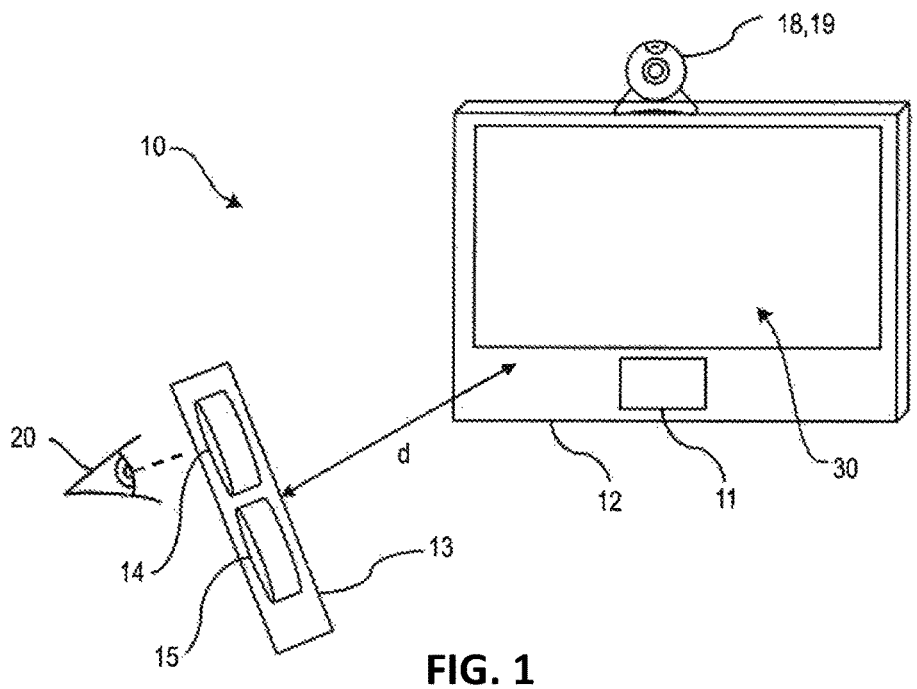
FIG. 1 shows an exemplary embodiment of a system for determining the subjective refraction properties of an eye of a subject based on the use of a natural image.

FIG. 1 shows an exemplary embodiment of a system for determining the subjective refraction properties of an eye of a subject based on the use of a natural image. The system is designated here in its entirety by the reference sign 10.

The system 10 for determining the subjective refraction properties of the subject's eye 20 includes the following: a memory device 11, in which at least one natural image 30 is stored; a display apparatus 12 for displaying the at least one natural image 30 from the memory device 11; and an optics arrangement 13 for setting different light-refracting elements 14, 15 into an optical path between the eye 20 of the subject and the display apparatus 12, wherein the optics arrangement 13 is arranged at a specified distance d from the display apparatus 12.

The memory device 11 in this exemplary embodiment can be integrated in the display apparatus 12 or be arranged physically separate from the display apparatus 11 and be connected thereto in wireless or wired fashion, as long as the natural image 30 stored in the memory device 11 can be displayed on the display apparatus 12.

The display apparatus 12 in the present exemplary embodiment is a flat-screen television set. The latter typically has a screen diagonal of no less than 55 inches. The display surface of the display apparatus can furthermore be curved to permit a more immersive representation of the natural image 30. The vision situation during the refraction determination is therefore closer to the typical vision conditions of the subject in his typical environment. The display apparatus can be a three-dimensional (3D) screen. One advantage of 3D representation is that the determination of the subjective refraction properties can be affected not only in monocular fashion in two-dimensional space, but optionally also in monocular fashion under bidirectional conditions. The representation of moving natural images in the form of video sequences is also possible. For 3D representation, known techniques such as shutter techniques or polarization filters can be used. The display apparatus 12 is optionally a holographic display.

The optics arrangement in the present exemplary embodiment is a phoropter, which is schematically illustrated in simplified form by way of two lens elements 14 and 15. Alternatively, measuring spectacles can be used, for example. In one exemplary embodiment of a method for the refraction determination, the subject is seated on an examination chair opposite the display apparatus 12 at a defined distance from the display apparatus 12 and observes the natural image 30 that is presented on the display apparatus 12 through the optics arrangement 13. An exemplary embodiment of a method sequence of the refraction determination will be explained in more detail below with reference to FIG. 11.

Provision may optionally furthermore be made for the system 10 to have means 18 for capturing the head movement and/or eye movement of the subject. In the exemplary embodiment shown, the system 10 has a camera 18 for this purpose, which is arranged on the display apparatus 12. Alternatively, movement sensors can be used, for example. Electrooculographic (EOG) determination of the eye movement is also possible.

Provision may furthermore be optionally made for the system 10 to have an eccentric photorefractor 19. The eccentric photorefractor 19 can be arranged on the display apparatus 12. Typically, a camera 18 is provided, which is not only part of the eccentric photorefractor 19, but also serves to capture the head movement and/or eye movement of the subject. It is thus possible to obtain a synergy effect.

Figure 2:
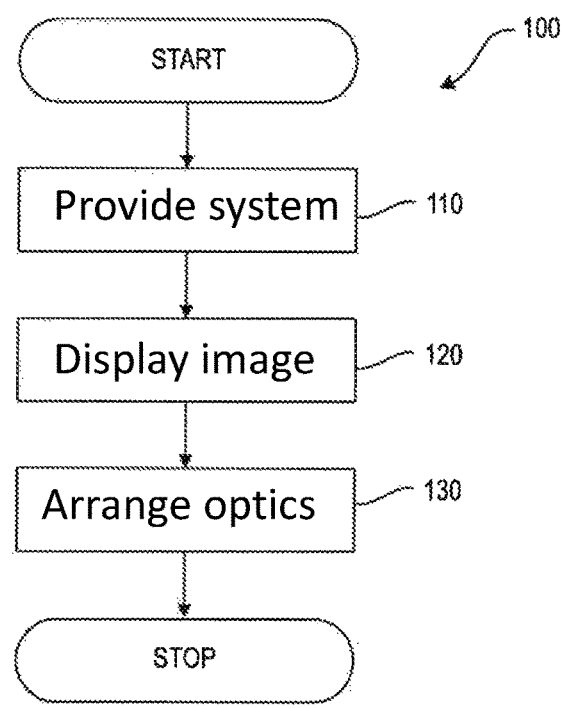
FIG. 2 shows an exemplary embodiment of a corresponding method.

FIG. 2 illustrates an embodiment of a method for determining the subjective refraction properties of an eye of a subject based on the use of a natural image. The method is denoted generally by 100.

The method 100 here has the following steps: In step 110, a system 10, as described by way of example above with reference to FIG. 1, is provided. In step 120, at least one natural image 30, which is stored in a memory device 11, is displayed on a display apparatus 12. It is also possible here for an image having a plurality of image regions to be stored in the memory device, wherein different image regions have different spatial frequencies and wherein the natural image depicts a natural scenery and said image is displayed on the display apparatus 12. In step 130, different light-refracting elements 14, 15 are set into an optical path between the subject's eye 20 and the display apparatus 12 using an optics arrangement 13, wherein the optics arrangement 13 is arranged at a specified distance d from the display apparatus 12. For an exemplary embodiment of a sequence of the refraction determination, reference is once again made to FIG. 11.

Figure 3:
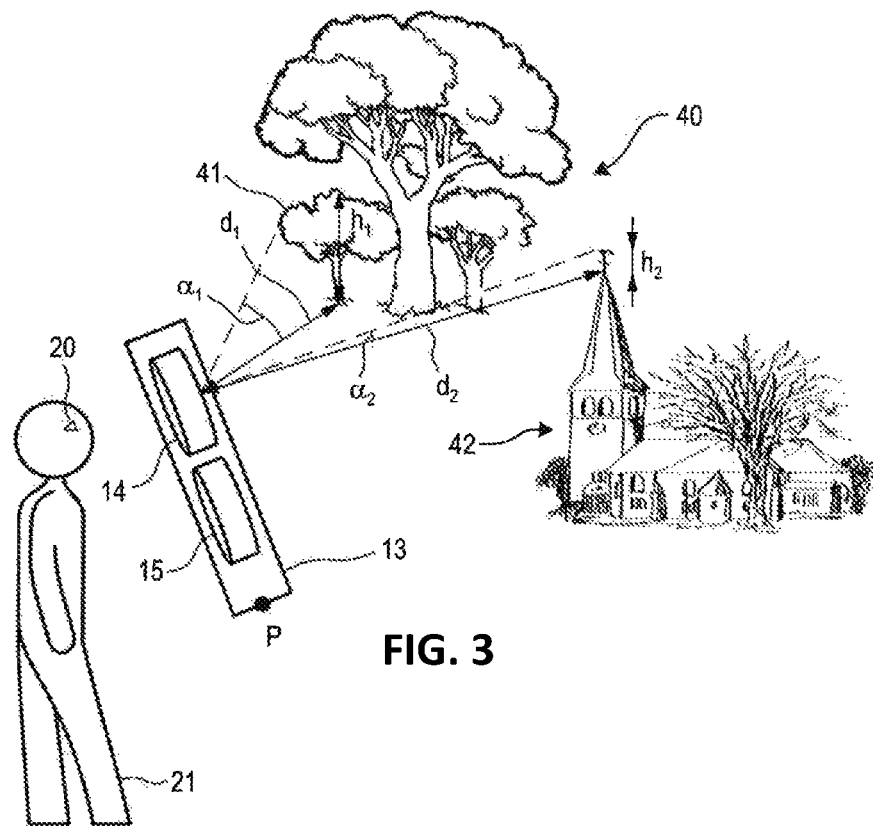
FIG. 3 shows an exemplary embodiment of a method for determining the subjective refraction properties of an eye of a subject on the basis of a natural scenery.

FIG. 3 shows an exemplary embodiment of a scenario for determining the subjective refraction properties of an eye 20 of a subject 21 on the basis of a natural scenery 40.

Figure 4:
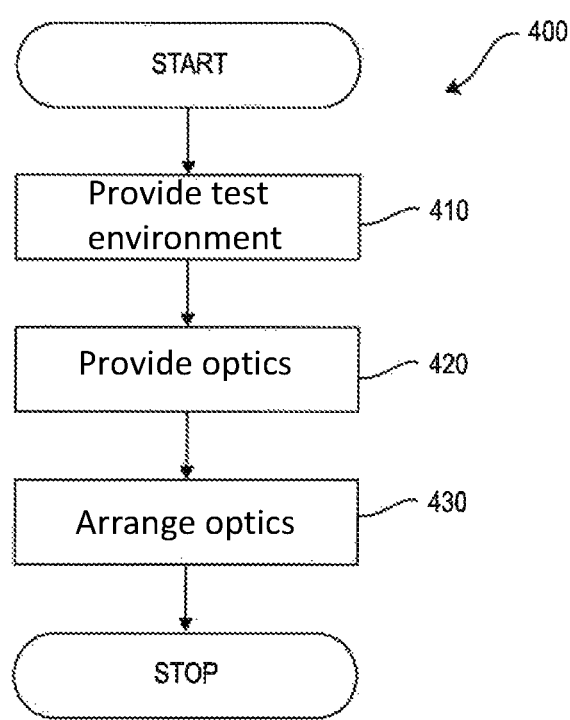
FIG. 4 shows an exemplary embodiment of a corresponding method.

FIG. 4 shows a corresponding method 400 for determining the subjective refraction properties of an eye 20 of a subject 21 based on the use of a natural scenery 40, wherein the method includes the following steps: In step 410, a test environment having the natural scenery 40 is provided, wherein the natural scenery, as viewed from a specified position P, has different regions of different spatial frequencies. In step 420, an optics arrangement 13 for setting different light-refracting elements 14, 15 into an optical path between the subject's eye 20 and the natural scenery is provided. In step 430, different light-refracting elements 14, 15 are set into the optical path between the subject's eye 20 and the natural scenery using the optics arrangement 13, wherein the optics arrangement 13 is arranged at the specified position P. For an exemplary sequence of the refraction determination, reference is once again made to FIG. 11.

The natural scenery 40 has, just like a natural image 30, features of different structure size, which correspond to different visual angles $\alpha_1$, $\alpha_2$ of the subject 21. In the example illustrated in FIG. 3, the natural scenery 40 includes a group of trees of different sizes. The height h1 of the tree 41 for example, viewed from the observation distance d1, corresponds to a visual angle $\alpha_1$. If the subject cannot detect the tree 41, his eye is not able to resolve the angle $\alpha_1$, at least not without the help of a light-refracting optical element 14, 15. For test purposes, different light-refracting elements 14, 15 can be introduced into the optical path between the subject's eye 20 and the tree 41. In this way, a refractive error of the subject's eye can be corrected and determined, and the subject may detect the desired structure, in the present case the tree 41. Further details are described with reference to FIG. 11.

The procedure can be repeated for further structures or elements of the natural scenery. Structures that become successively smaller are typically used. This results in an approximation to the resolution threshold of the subject. In the case of the church 42, the subject can, for example, be asked, one after the other, what type of building is depicted, how many windows the tower has and what object is located at the top of the spire. For example, if the subject can see the weathercock on the church spire, then this corresponds, with the height of the weathercock $h_2$ from the observation distance $d_2$, to a resolution capability of at least the visual angle $\alpha_2$. In other words, the determination of the subjective refraction properties can be affected not only using a display apparatus on which a natural image is displayed, but directly by viewing a natural scenery through the optics arrangement. The following statements relating to natural images correspondingly apply.

Figure 5:
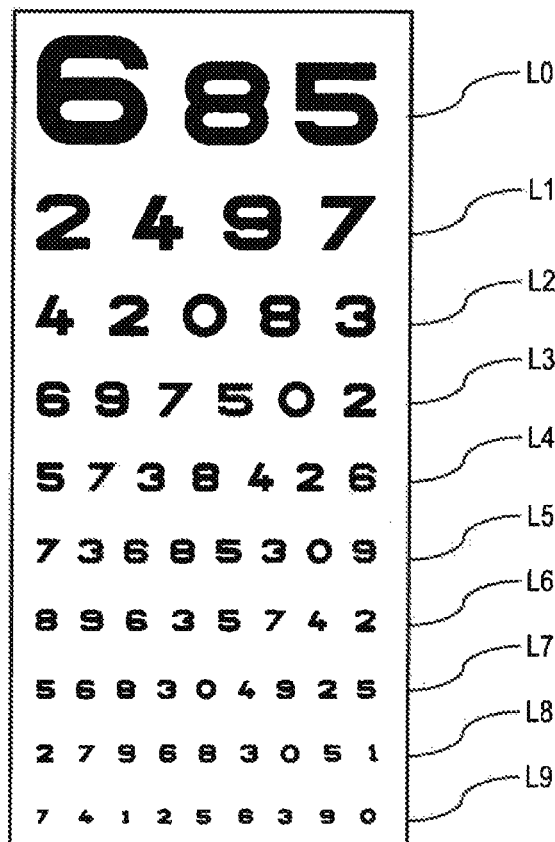
FIG. 5 shows an example of a conventional eyesight testing chart.

FIG. 5 shows an example of a conventional eyesight testing chart. The eyesight test symbols used here are numbers. However, other eyesight test symbols, such as what are known as Landolt rings or the tumbling E, are also customary. The eyesight testing chart has ten lines L0 to L9 with numbers of different sizes. In practice, the complete individual optotypes are always used for the determination of the visual acuity. In the present example, the subject is therefore asked about individual numbers one after the other and independently of one another.

Figure 6:
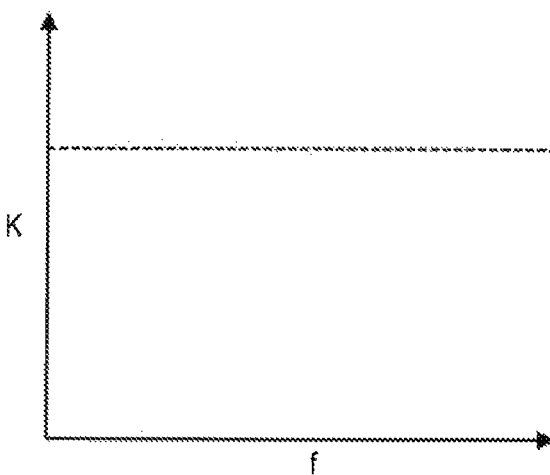
FIG. 6 shows a schematic of the contrast over the spatial frequency for conventional eyesight testing charts.

Independently of the size, the eyesight test symbols are shown in black on a white background. FIG. 6 illustrates a corresponding schematic of the contrast over the spatial frequency for conventional eyesight testing charts. In accordance with national and international standards, the contrast needs to be very high, ideally equal to 1 in accordance with Michelson, specifically for all tested sizes of the vision symbols and thus for all spatial frequencies used. As shown in FIG. 6, the contrast is constant with respect to the spatial frequency and independently of the size the same for all eyesight test symbols.

If an eyesight testing chart, or eye chart, as is shown by way of example in FIG. 5, is used, the individual lines are used to define refractive errors of the eye and therefore an optimum spectacle strength which compensates for any refractive error present. In particular, if an eyesight testing chart is used, the visual acuity of the subject is tested using different light-refracting elements of the optics arrangement in the individual rows, and the light-refracting elements are changed such that it is possible for the subject to be able to discern a smallest possible row. If the eyesight testing chart from FIG. 5 is used for an image size of 998 pixels in height and 2120 pixels in width at a distance of 1 m on a screen having a pixel resolution of 0.0275 centimeters per pixel [cm/px], the following visual acuity values are obtained for the rows L1-L9 in accordance with table 1. In addition to statements relating to the pixel dimension, the required minimum resolution capability [logMAR] for being able to discern a detail is given.

TABLE 1

| Line | Pixel height of the symbol | Minimally required resolution capability [visual acuity] | Minimally required visual acuity [logMAR] |
| --- | --- | --- | --- |
| L1 | 137 | 0.04 | 1.41 |
| L2 | 102 | 0.05 | 1.29 |
| L3 | 86 | 0.06 | 1.21 |
| L4 | 70 | 0.08 | 1.12 |
| L5 | 60 | 0.09 | 1.05 |
| L6 | 52 | 0.10 | 0.99 |
| L7 | 48 | 0.11 | 0.96 |
| L8 | 43 | 0.12 | 0.91 |
| L9 | 33 | 0.16 | 0.80 |

Figure 7:
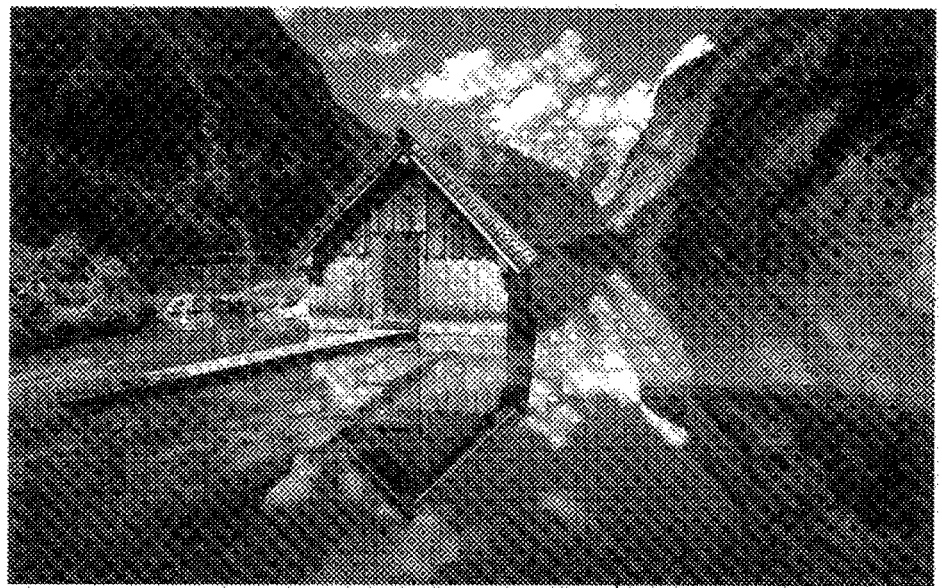
FIG. 7 shows an exemplary embodiment of a natural image.

In contrast to a conventional eyesight testing chart, FIG. 7 shows an exemplary embodiment of a natural image 30. In the present exemplary embodiment, the natural image 30 typically corresponds to a photograph of a typical rural environments in which the subject lives. Depicted are a cabin or a boathouse at the edge of a lake against the background of mountains.

The characteristic parameters of natural images follow specific rules. The spatial contents of a natural image can be mathematically calculated, for example, by a Fourier transform. For example, in MATLAB® software, the command FFT2 can be used here. In dependence on the pixel density on a computer monitor and the viewing distance from the monitor, it is ascertained what spatial frequencies are present in an image.

Figure 8:
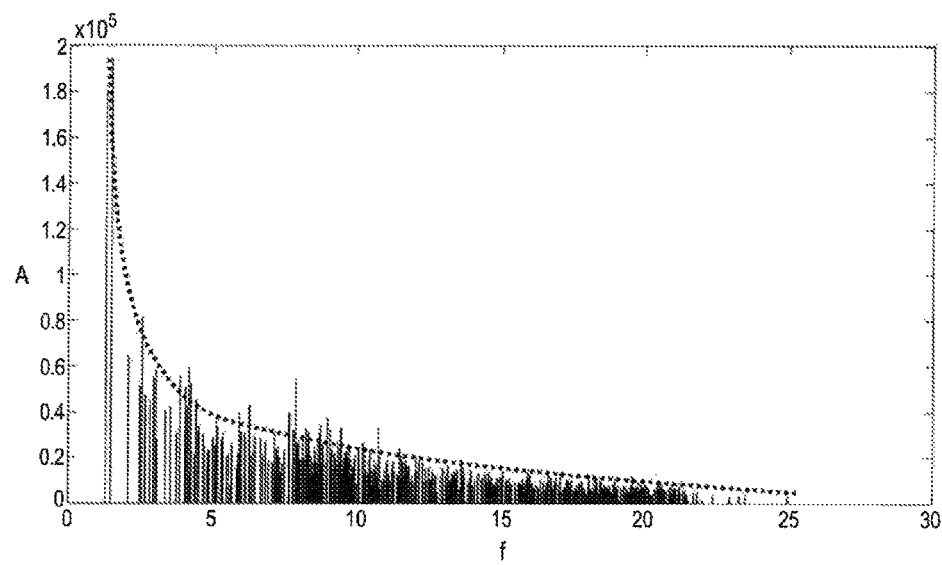
FIG. 8 shows a spatial frequency diagram of the natural image of FIG. 7.

FIG. 8 shows a spatial frequency diagram of the exemplary embodiment of the image of FIG. 7. The horizontal axis gives the spatial frequency f in cycles per degree, and the vertical axis gives the number of the corresponding spatial frequencies A. The illustration in FIG. 8 corresponds to a spatial frequency analysis or Fourier transform of the image from FIG. 7, if it is viewed in a size of 1920 pixels in width and 1200 pixels in height at a distance of 1 m with a pixel resolution of 0.0275 centimeters per pixel [cm/px]. FIG. 6 gives the number of different spatial frequencies for the y-direction, that is to say the vertical direction, of the depiction in FIG. 5. A natural image can occasionally be characterized by the fact that the number of spatial frequencies, or an amplitude of the spatial frequency diagram, decreases as the spatial frequency increases. This tendency is illustrated in FIG. 8 by way of the dashed line. In particular, the amplitude of the spatial frequency diagram in a natural image is inversely proportional to the spatial frequency (see also Tolhurst et al. "Amplitude spectra of natural images," Ophthal. Physiol. Opt., Vol. 12, 1992, and also Field et al. "Relations between the statistics of natural images and the response properties of cortical cells," Vol. 4, No. 12, Journal of the Optical Society of America, 1987).

When using a conventional eyesight testing chart, as in FIG. 5, the individual lines with individual eyesight test symbols are used for determining the subjective refraction properties or the spectacle strength. In contrast, when using a natural image, as in FIG. 7, different image regions or different image contents can be used. Using a spatial frequency analysis, it is typically possible to deduce the image content. From the spatial frequency of features or image contents in the natural image, a transformation to the visual acuity can be affected.

Figure 9:
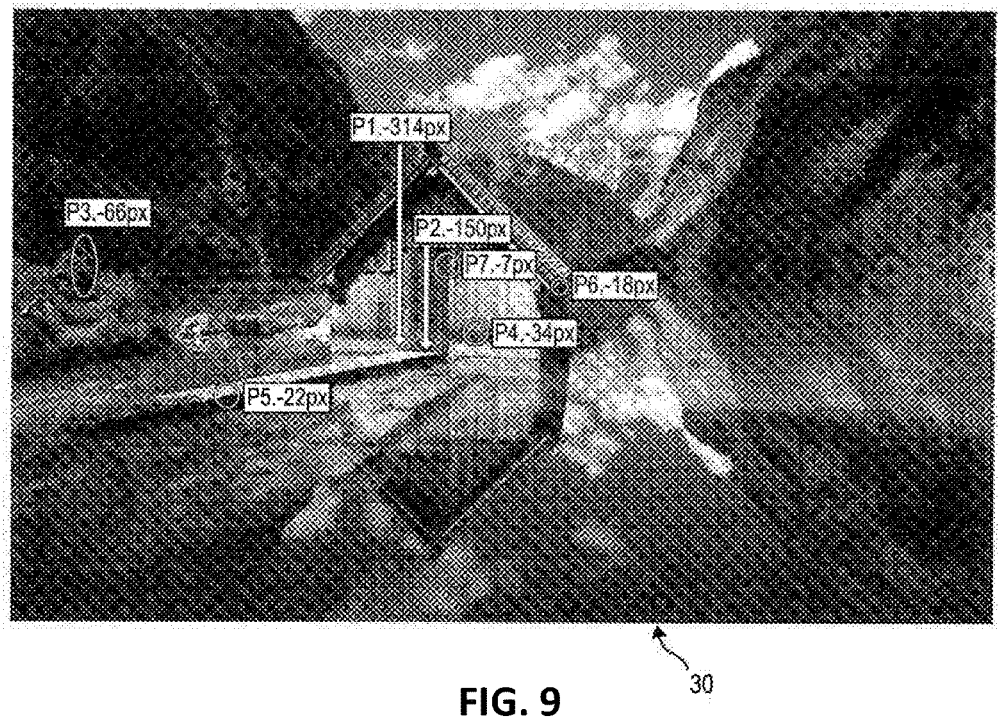
FIG. 9 shows the natural image from FIG. 7 with notations of regions of different spatial frequencies.

For a better illustration, FIG. 9 once again shows the exemplary embodiment of image 30 from FIG. 7 with notations of regions of different spatial frequencies. Here, different details of the image are defined by positions P1 to P7 in the image. The corresponding pixel dimensions are here also given by way of their pixel number for the different details which were selected as examples. The selected details can be what are known as regions of interest (ROIs), which are used for asking the subject questions during the habitual refraction determination.

The following exemplary table indicates how great the visual acuity of the eye must be to be able to discern the details at an image size of 1920 pixels in width and 1200 pixels in height for a distance of one meter and a pixel resolution of the display apparatus 12 of 0.0275 centimeters per pixel [cm/px].

TABLE 2

| Position | Pixel number | Minimally required resolution capability [visual acuity] | Minimally required visual acuity [logMAR] |
|---|---|---|---|
| P1 | 314 | 0.0158 | 1.8 |
| P2 | 150 | 0.315 | 1.5 |
| P3 | 66 | 0.08 | 1.10 |
| P4 | 34 | 0.16 | 0.80 |
| P5 | 22 | 0.25 | 0.6 |
| P6 | 18 | 0.3 | 0.5 |
| P7 | 7 | 0.8 | 0.1 |

Figure 10:
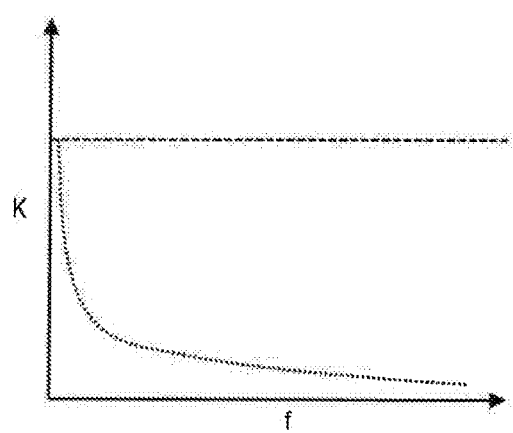
FIG. 10 shows a schematic of the contrast over the spatial frequency for an image in accordance with the present disclosure.

FIG. 10 shows a schematic of the contrast K over the spatial frequency f for an image in accordance with the present disclosure. In contrast to a conventional eyesight testing chart, which has a constant contrast with respect to the spatial frequency, it is proposed in the present disclosure in particular to use images for the refraction determination, in which the contrast decreases as the spatial frequency increases. To determine the contrast, the gray level of a pixel can be compared to the gray level of its neighboring pixel. The contrast can in particular be inversely proportional to the spatial frequency.

In other words, a further rule for the proposed natural images lies in the decrease in contrast as the spatial frequency increases. When evaluating different natural images, for example Tolhurst et al. (Tolhurst, D. J., Tadmor, Y., & Chao, T. (1992). Amplitude spectra of natural images. Ophthalmic and Physiological Optics, 12(2), 229-232.) showed that the slope of the decrease as the spatial frequency increases is on average −1.2. This correlation is also described by Burton et. al. (Burton et. al., "Color and spatial structure in natural scenes," Applied Optics, Vol. 26, No. 1, 1987).

Figure 11:
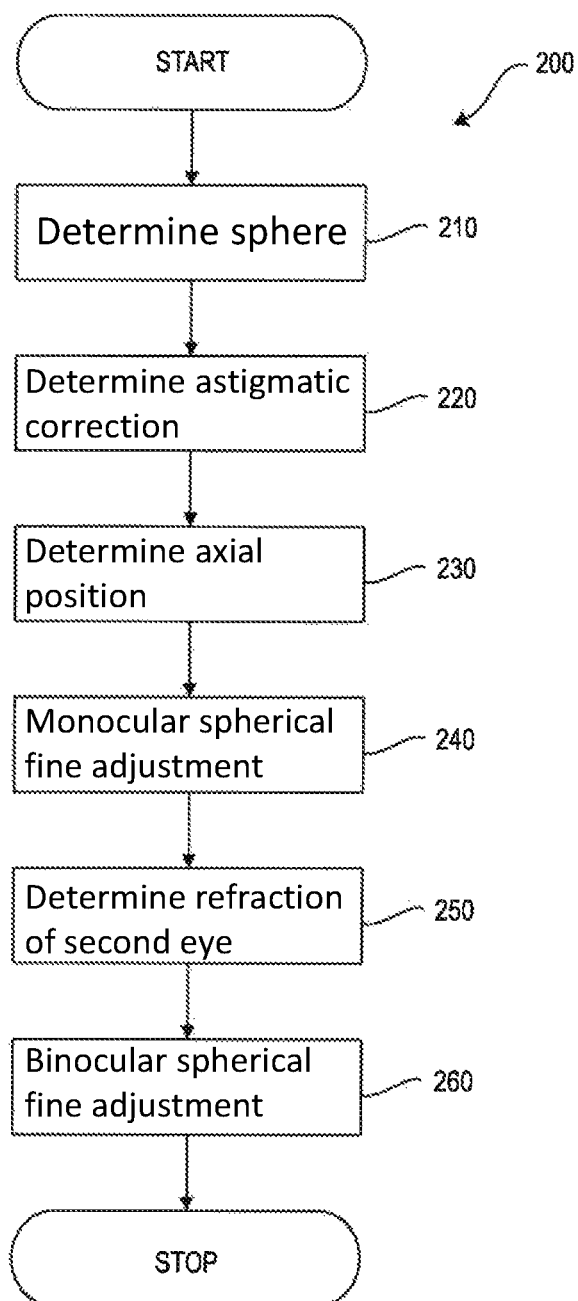
FIG. 11 shows an exemplary embodiment of a method for determining the subjective refraction properties of an eye of a subject.

FIG. 11 shows an exemplary embodiment of a method for determining the subjective refraction properties of an eye 20 of a subject. Using the natural image from FIG. 7 or FIG. 9, or in a scenario with a natural scenery as in FIG. 3, the refraction determination can be performed as follows:

In step 210, initially a required sphere of the subject can be determined. The subject is not wearing his own correction and views the natural image 30 shown on the display apparatus 12 through the optical unit 13, in the present case through a phoropter. For example, the subject is initially required to discern details in accordance with position 1 (house). If he is unable to do so, initially a plus lens (in accordance with grading table) is placed in front of him and he is asked if this is worse. If not, correction can continue with plus lenses until a satisfactory result is attained. If yes, minus lenses are used to correct further. Subsequently, lenses in accordance with the grading table and increasingly smaller details from the image can be used. If the customer, for example, can discern position 7 (door fitting) in the image, the desired or best spherical lens has been found.

The following table shows a grading table for spherical lenses. The grading table gives a grading of the lenses to be held up or to be added during the determination of spherical corrections in dependence on the visual acuity.

TABLE 3

| Visual acuity | Lens grading in diopters (dpt) |
|---|---|
| under 0.05 | 2 dpt |
| 0.05 to 0.2 | 1 dpt |
| 0.2 to 0.5 | 0.5 dpt |
| over 0.5 | 0.25 dpt |

In step 220, an astigmatic correction can be determined. Once the best spherical lens has been found, the test for astigmatism takes place. For example, the subject can be asked to view position 5. A cross cylinder (grading in accordance with grading table) is introduced, and he is asked if this is better or worse. It is thus possible to once again ask questions while placing lenses in front of the subject. Depending on the answer, an astigmatism is determined and a corresponding correction is used (yes) or not (no). The questions relating to lenses can continue until the questions yield no improvement or worsening. Care should be taken here to ensure that the spherical error is followed (in accordance with grading table).

In step 230, an axial position of the astigmatic correction can be determined. Here, the exact axial position of the correcting cylindrical lens can be found by way of a lens flipping examination. For example, the subject will be asked here to look at position 3 (plant). The lens flipping examination is continued until the customer sees no difference between the two axial positions during the lens flipping examination.

In step 240, a monocular spherical fine adjustment can be performed, in particular after the performance of steps 210 to 230. To this end, the subject can be asked to view position 6. Plus lenses or minus lenses can be held up until the highest visual acuity, i.e., the greatest visual acuity, with maximum plus is achieved.

In step 250, a refraction determination of the second eye can be performed analogously to the previously described steps 210 to 240.

In step 260, a binocular spherical fine adjustment can be performed. To this end, step 240 can be performed under binocular conditions. To this end, the client can view, for example, the clouds in the sky.

Optionally, a determination of measurement values from a measurement and correction methodology in accordance with Haase with conventionally known tests can be performed subsequently to the ascertainment of lower order refraction errors, such as sphere, astigmatism and cylinder.

The foregoing description of the exemplary embodiments of the disclosure illustrates and describes the present invention. Additionally, the disclosure shows and describes only the exemplary embodiments, but, as mentioned above, it is to be understood that the invention is capable of being used in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents, and patent applications cited in this specification are herein incorporated by reference, and for any and all purposes, as if each individual publication, patent, or patent application were specifically and individually indicated to be incorporated by reference. In the case of inconsistencies, the present disclosure will prevail.

The invention claimed is:

1. A system for determining the subjective refraction properties of an eye of a subject based on a utilization of a natural image, the system comprising:
   a memory device configured to store at least one natural image;
   a display apparatus configured to display the at least one natural image stored in the memory device; and
   an optics arrangement configured to insert at least one light-refracting element from a plurality of light-refracting elements into an optical path between the subject's eye and the display apparatus;
   wherein the optics arrangement is arranged at a predetermined distance from the display apparatus, and
   wherein the natural image includes at least two regions having different spatial frequencies, respectively, and
   wherein the natural image depicts a natural scenery.

2. The system as claimed in claim 1, wherein the natural image has a spatial-frequency-dependent contrast, and
   wherein the contrast decreases as the spatial frequency increases.

3. The system as claimed in claim 2, wherein the contrast is inversely proportional to the spatial frequency.

4. The system as claimed in claim 2, wherein the contrast of the natural image is elevated for higher spatial frequencies.

5. The system as claimed in claim 1, wherein the natural image comprises a distribution of spatial frequencies including a plurality of spatial frequencies required for determining subjective refraction properties of the subject's eye in one image.

6. The system as claimed in claim 1, wherein the natural image depicts structures with different spatial frequencies, and
   wherein the spatial frequency distribution, upon observation at the predetermined distance, includes at least one spatial frequency of less than or equal to 0.3 cycles per degree and at least one spatial frequency greater than or equal to 60 cycles per degree.

7. The system as claimed in claim 1, further comprising:
   a selection device for selecting the natural image in accordance with a preference of the subject.

8. The system as claimed claim 1, wherein the natural image includes at least one alien component.

9. The system as claimed in claim 1, wherein at least one vision symbol is at least partially integrated in the natural image.

10. The system as claimed in claim 1, wherein the display apparatus has a curved display surface.

11. The system as claimed in claim 1, further comprising means:
   for capturing a head movement of the subject, an eye movement of the subject, or the head movement and the eye movement.

12. The system as claimed in claim 1, wherein the natural image is a video.

13. The system as claimed in claim 1, further comprising: an eccentric photorefractor.

14. A method for determining subjective refraction properties of an eye of a subject perceiving a natural image, the method comprising:
   providing a system configured to determine the subjective refraction properties of an eye of a subject perceiving a natural image, the system including:
      a memory device configured to store at least one natural image;
      a display apparatus configured to display the at least one natural image stored on the memory device; and
      an optics arrangement configured to insert at least one light-refracting element from a plurality of light-refracting elements in an optical path between the subject's eye and the display apparatus;
   arranging the optics arrangement at a predetermined distance from the display apparatus;
   displaying the at least one natural image stored in the memory device on the display apparatus;
   placing different light-refracting elements from the plurality of light elements in the optical path between the subject's eye and the display apparatus with the optics arrangement; and
   providing the natural image with at least two regions having different spatial frequencies, wherein the natural image depicts a natural scenery.

15. The system as claimed in claim 4, wherein the contrast of the natural image is elevated to a contrast level of the natural scenery depicted by the natural image.

16. The system as claimed in claim 5, wherein the distribution of spatial frequencies includes all spatial frequencies required for determining subjective refraction properties of the subject's eye in one image.

17. The system as claimed in claim 6, wherein the natural image depicts structures with different spatial frequencies, wherein the spatial frequency distribution, upon observation at the predetermined distance, has at least one spatial frequency of less than or equal to 0.01 cycles per degree and at least one spatial frequency greater than or equal to 80 cycles per degree.

18. A system for determining the subjective refraction properties of an eye of a subject based on a utilization of a natural image, the system comprising:
   a memory device configured to store at least one natural image;
   a display apparatus configured to display the at least one natural image stored in the memory device; and
   an optics arrangement configured to insert at least one light-refracting element from a plurality of light-refracting elements into an optical path between the subject's eye and the display apparatus;
   wherein the optics arrangement is arranged at a predetermined distance from the display apparatus, and
   wherein the natural image includes a plurality of image regions, wherein different image regions have different spatial frequencies and wherein the natural image depicts a natural scenery.

19. A method for determining subjective refraction properties of an eye of a subject perceiving a natural image, the method comprising:
   providing a natural image with a plurality of image regions;
   displaying the natural image to the subject at a first distance;
   arranging a first light-refracting element at a second distance in an optical path between the subject's eye and the natural image;
   replacing the first light-refracting element with a second light-refracting element at the second distance in the optical path between the subject's eye and the natural image;
   receiving a description of at least one image region from among the plurality of image regions from the subject; and
   determining the subjective refraction properties of the eye of the subject perceiving the natural image, wherein different image regions from among the plurality of image regions have different spatial frequencies and wherein the natural image depicts a natural scenery.

* * * * *